United States Patent [19]

Wade

[11] 4,250,266
[45] Feb. 10, 1981

[54] AUTOMATED MICRO-ORGANISM CULTURE GROWTH AND DETECTION INSTRUMENT

[75] Inventor: Gerald J. Wade, Littleton, Colo.

[73] Assignee: Honeywell Inc., Minneapolis, Minn.

[21] Appl. No.: 105,376

[22] Filed: Dec. 19, 1979

[51] Int. Cl.³ .............................................. C12M 1/36
[52] U.S. Cl. ........................................ 435/289; 435/3; 435/290; 435/291; 435/809; 204/195 B; 422/67
[58] Field of Search ....................... 435/291, 3, 29, 31, 435/32, 33, 34, 36, 37, 38, 289, 290, 809

[56] References Cited
U.S. PATENT DOCUMENTS

| | | | |
|---|---|---|---|
| 3,618,734 | 11/1971 | Khan | 435/809 X |
| 3,743,581 | 7/1973 | Cady et al. | 435/34 |
| 4,090,921 | 5/1978 | Savamura et al. | 435/809 X |

*Primary Examiner*—Robert J. Warden
*Attorney, Agent, or Firm*—L. J. Marhoefer; Lockwood D. Burton; Mitchell J. Halista

[57] ABSTRACT

An automated micro-organism culture growth and detection apparatus includes a plurality of carousel trays arranged in pairs, providing receptacles for a plurality of culture bottles. The bottles each include a pair of electrodes submerged in the culture liquid and extend through an end wall of the bottle to form contact points. The receptacles include a pair of spring finger electrical contacts for each bottle to connect the electrodes to a measuring circuit. The complementary sets of the pairs of carousel trays are driven in counter-rotational directions to provide agitation for the culture during incubation and to index the individual to an access door in the incubation chamber surrounding the assembled carousel trays. A continuous flow of air at a controlled temperature is caused to flow through the incubation chamber which, together with the agitation, promotes the rapid growth of micro-organism in the culture bottles. The operation of the entire system including the driving of the carousel trays and the measuring of the growth characteristics of the micro-organisms is under the control of a micro-computer.

16 Claims, 12 Drawing Figures

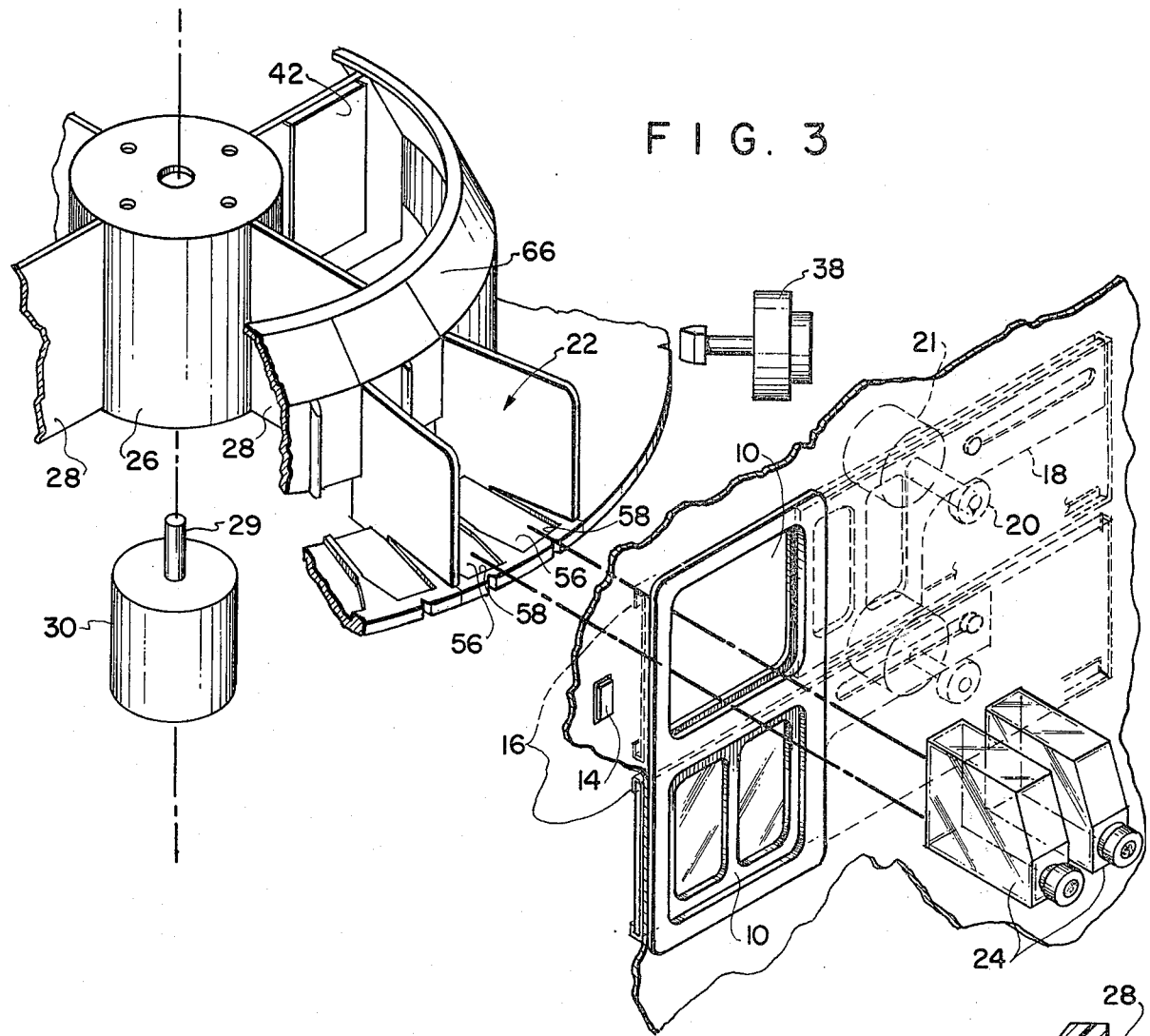
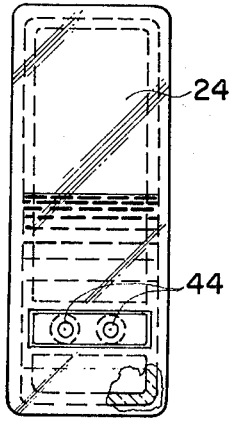
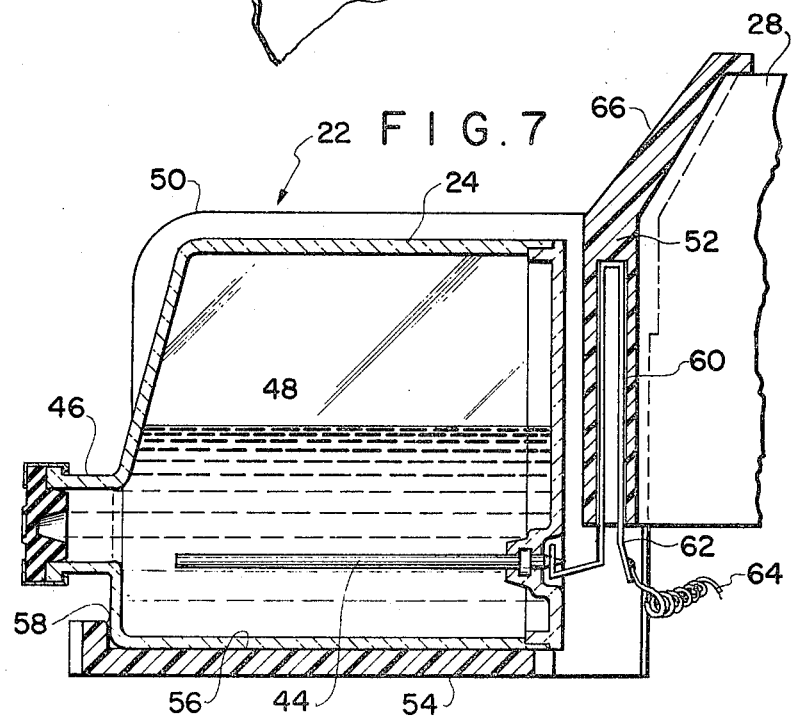

AUTOMATED MICRO-ORGANISM CULTURE GROWTH AND DETECTION INSTRUMENT

BACKGROUND OF THE INVENTION

The present relates to medical instrumentation. More particularly it relates to a micro-organism culture apparatus.

There is a growing need for the ability to rapidly determine the existance of a micro-organism in a substance such as human blood. To accomplish the detection of such organisms, a sample of the substance to be tested is placed in a culture medium, incubated, then examined after a predetermined period of incubation, for a growth of the micro-organism. This examination may be accomplished by a physical examination by an experienced operator. In other apparatus, the culture is examined optically by suitable electronic apparatus. Other means have been provided for measuring the growth of micro-organisms by means of electrodes extending into the culture liquid and detecting a change in the electrical characteristics of the liquid as a function of the micro-organism growth, or by radio isotope detection.

Those techniques which have depended upon the observation by an operator have been expensive, slow, and rely on the judgment of the human operator. Those systems which are based on electro-optical techniques are also slow. Among other things, the optical techniques require that the culture be kept mechanically quiescent to avoid obscuring the optical response wherein the detection is of a visible colony growth. The quiescent state of the culture results in a relatively slow growth of the micro-organism colonies, resulting in a relatively slow analysis program. These techniques have not been entirely satisfactory especially in the growing demands for a faster response time whereby to enable an earlier diagnosis of viable organisms.

The systems based on electronic detection of the growth have required complex circuitry complete with reference cells and bridge detectors. Some of those are not suitable for use with a blood culture because of the unavailability of the reference sample of normal blood from the same patient. Radioisotope detection systems are also slow. Further, some micro-organisms do not carry the isotope into the multiplication process. Further, none of the foregoing techniques have been subjected to a fully automated incubation and detection system.

SUMMARY OF THE INVENTION

It is, accordingly, an object of the present invention to provide an improved micro-organism growth detection apparatus.

It is another object of the present invention to provide an improved, fully automatic, micro-organism culture incubation and detection apparatus.

It is a further object of the present invention to provide an improved apparatus as set forth which does not rely upon human judgment, which is accurate, reliable and fast in operation.

In accomplishing these and other objects, there has been provided, in accordance with the present invention, a micro-organism culture incubation and growth detection apparatus wherein a plurality of culture bottles each containing a nutrient medium and an innoculum which may or may not include a micro-organism are carried on a carousel type tray. The bottle is especially configured and includes a pair of submerged electrodes. The carousel tray includes receptacles for the reception of the bottles with each receptacle having pairs of electrical contacts in engagement with the external ends of the electrodes in the bottles. The carousel trays are encased in pairs in a closed incubation chamber. The trays are arranged to be driven in a counter-rotational relation about a central axis and may be indexed to present selected bottle receptacles to a controlled access port. Additionally, the trays are arranged to be driven in a counter-rotational oscillatory motion to provide agitation to the bottle contents thereby to accelerate the growth of any micro-organisms present. The incubation chamber is also provided with a continuous stream of warm air circulating about the culture bottles. The indexing of the trays, the periodic measurement of the electrical parameters of the content of each bottle and the display of the result of that measurement is accomplished under the control of a microprocessor.

BRIEF DESCRIPTION OF THE DRAWINGS

A better understanding of the present invention may be had from the following detailed description when read in the light of the accompanying drawings in which:

FIG. 3 is an exploded view of certain details of the interior structure of the apparatus shown in FIG. 2;

FIG. 7 is a cross-sectional view of the detail of the structure constructed in accordance with the present invention;

FIG. 8 is an end view of the bottle shown in FIG. 6;

DETAILED DESCRIPTION

Figure 1:
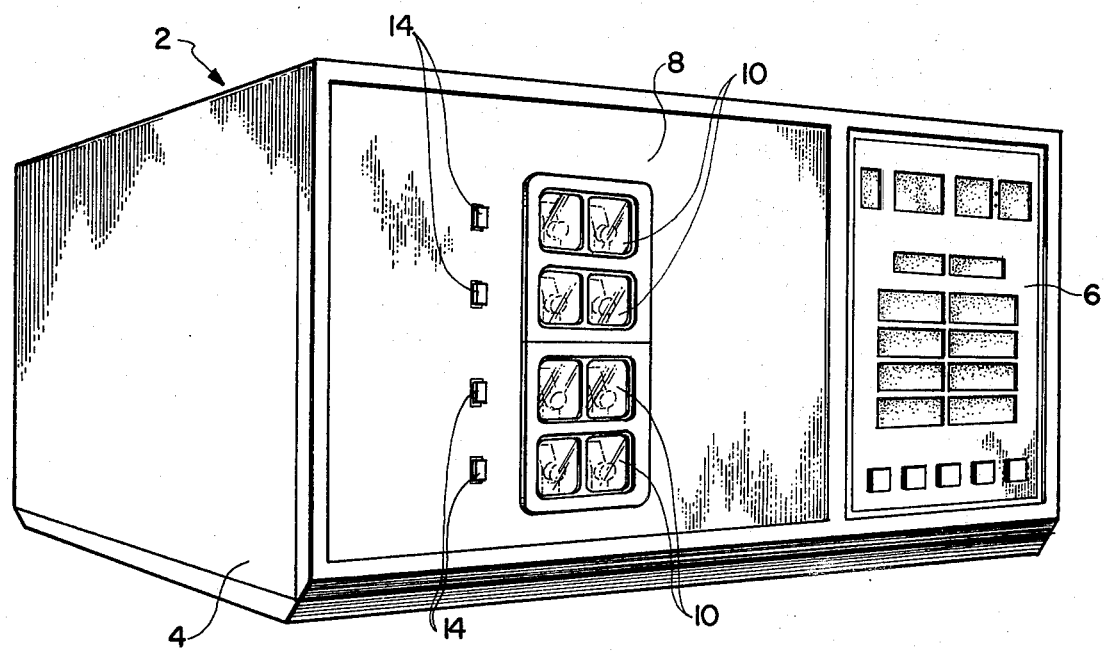
FIG. 1 is a perspective view of a micro-organism culture apparatus constructed in accordance with the present invention.
Figure 2:
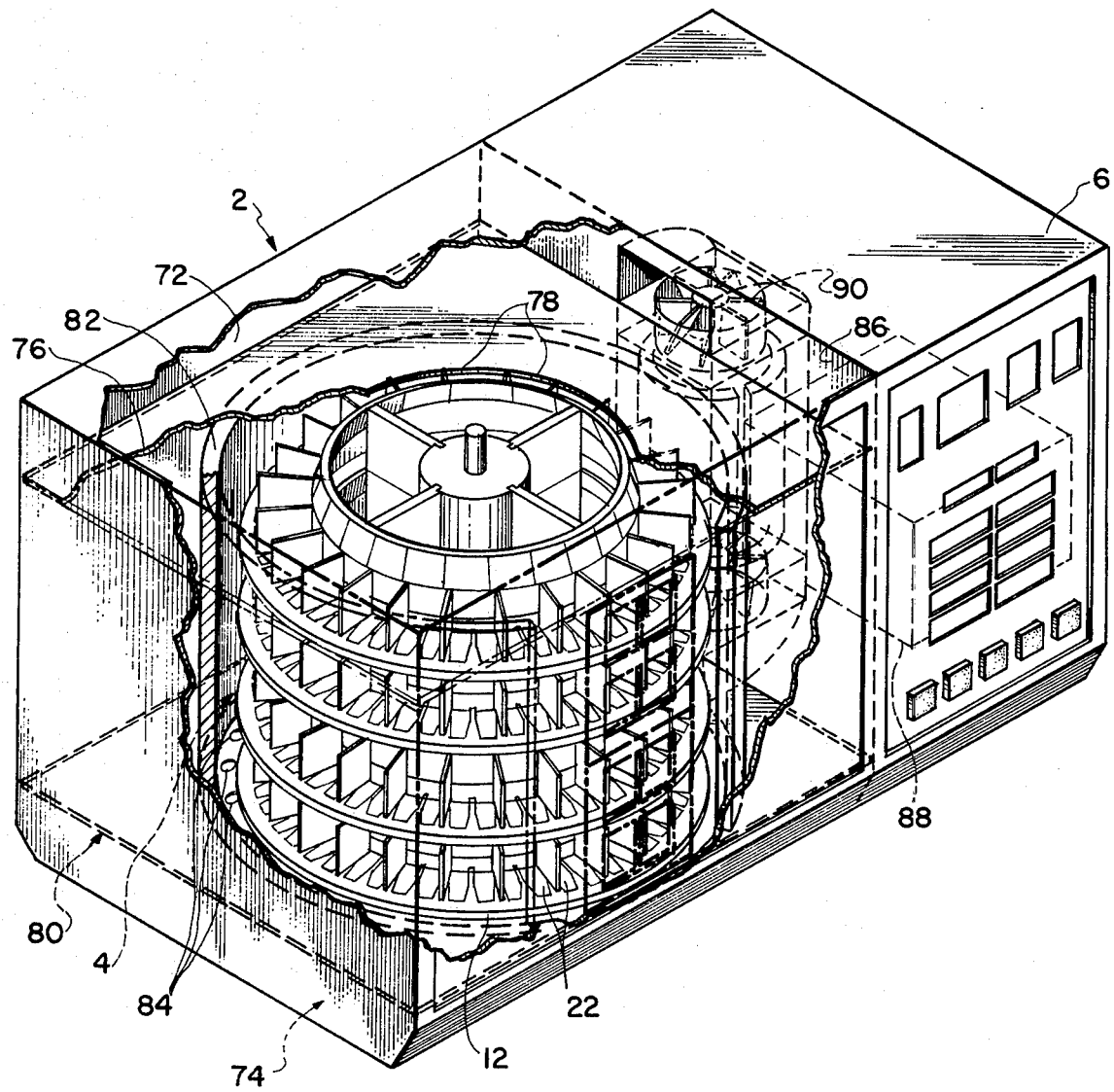
FIG. 2 is a perspective view of the apparatus shown in FIG. 1 with the exterior shown in phantom to illustrate the interior structure.
Figure 6:
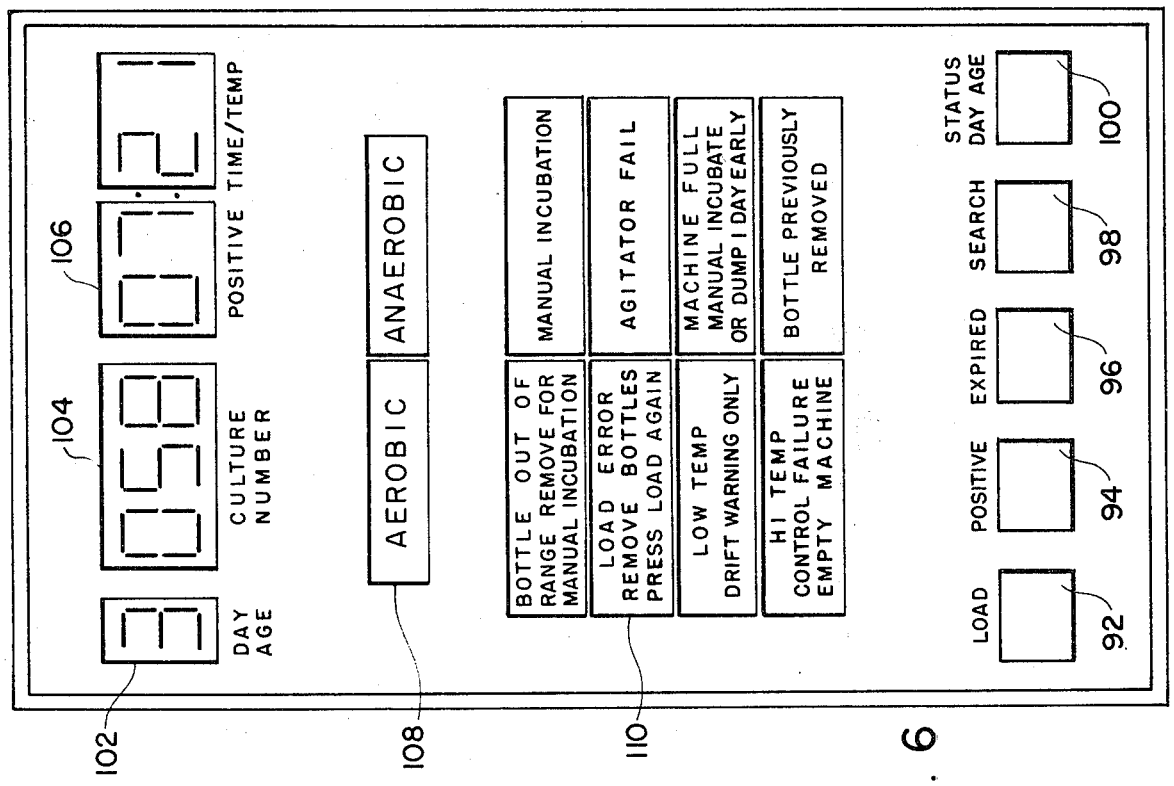
FIG. 6 is an illustration of the display and control panel of the apparatus constructed in accordance with the present invention.

Referring now to the drawings in greater detail, there is shown a micro-organism culture instrument constructed in accordance with the present invention. The structure includes a main housing 2 which encloses an incubation chamber 4 and a control compartment 6. The front panel 8 of the incubator compartment 4 includes a plurality of selectively operable doors 10. In the illustrative embodiment shown in FIGS. 1 and 2, there are four such doors shown. Interiorly of the incubation chamber 4, there is provided a plurality of circular tray assemblies or carousels 12. Again in the illustrative embodiment, there are four such carousels shown. Thus, each of the doors 10 in the front panel 8 in the incubation compartment 4 is aligned with and is adapted to cooperate with a corresponding one of the carousels 12. Adjacent each of the doors 10 is a signal light 14. As will be seen hereinafter, when one of the doors 10 has been programmed to be opened, the adjacent signal light 14 corresponding thereto will be lit. Each of the doors may be separately addressed to be selectively opened in response to control signals supplied thereto from the controlling apparatus, as will be seen hereinafter. The doors are arranged for sliding operation, as shown in FIG. 3. Each of the doors 10 are mounted for sliding operation in a bracket 16 and includes an operating arm extension 18. The operating arm 18 is engaged by a driving member 20 which may be in the form of a friction wheel or, alternatively, a pinion gear. In the latter case, the operating arm 18 would carry a rack gear to cooperate with the driving pinion. The driving member 20 is selectively operated by a small motor 21 which is, in turn, selectively energized from the control apparatus.

Figure 9:
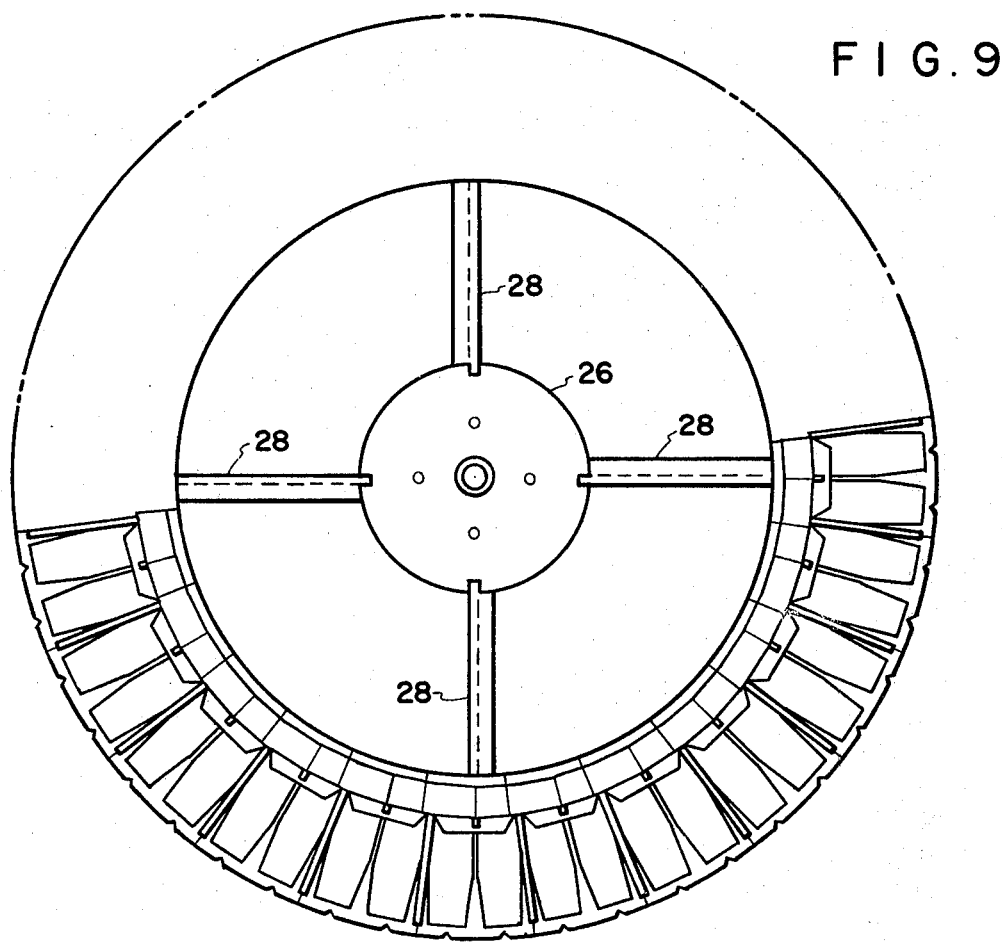
FIG. 9 is a top view of an element of the structure constructed according to the present invention.

Each of the carousel members, as may be more clearly seen in FIGS. 3 and 9, are formed with a plurality of receptacles 22 opening radially about the outer perimeter and forming effectively a torus about the axis of the carousel. Each of the receptacles 22 receives two culture bottles 24 of the type set forth in the aforementioned copending application, Ser. No. 079,696. These culture bottles are supplied in pairs to the machine inasmuch as, although the bottles are identical in physical structure, the contents of the bottle are such that one of the two bottles is arranged for anaerobic growth conditions. The other bottle is arranged for aerobic growth conditions. Thus, a sample of an innoculum having unknown micro-organism content is injected into both bottles to provide a growth environment for micro-organisms of either type. In an exemplary apparatus constructed in accordance with the present invention, each of the carousels were provided with twenty four receptacles with a capacity for forty eight culture bottles or twenty four pairs of culture bottles.

The torus or ring formed by the receptacles 22 is supported from a central hub 26 by a plurality of radial arms 28, four such arms being shown in the illustrative example. The carousels are arranged in the incubation chamber in pairs. That is, there is provided an equal number of trays in an upper carousel set and in a lower carousel set. The upper set of carousels are arranged to be driven in a counter-rotational direction relative to the lower set of carousels. Thus, it is contemplated that apparatus of the type herein set forth may include two, four, or six carousels with one, two or three carousels in each of the upper and lower sets. The carousels or trays 12 in the lower set are mechanically coupled together. Similarly, the trays or carousels 12 in the upper set are mechanically coupled together but not coupled to the lower set. In one embodiment of the present invention, the upper set of carousels were coupled to be driven by the shaft 29 of a drive motor 30 while the lower set were coupled to be driven by the housing of the same motor 30.

Figure 4:
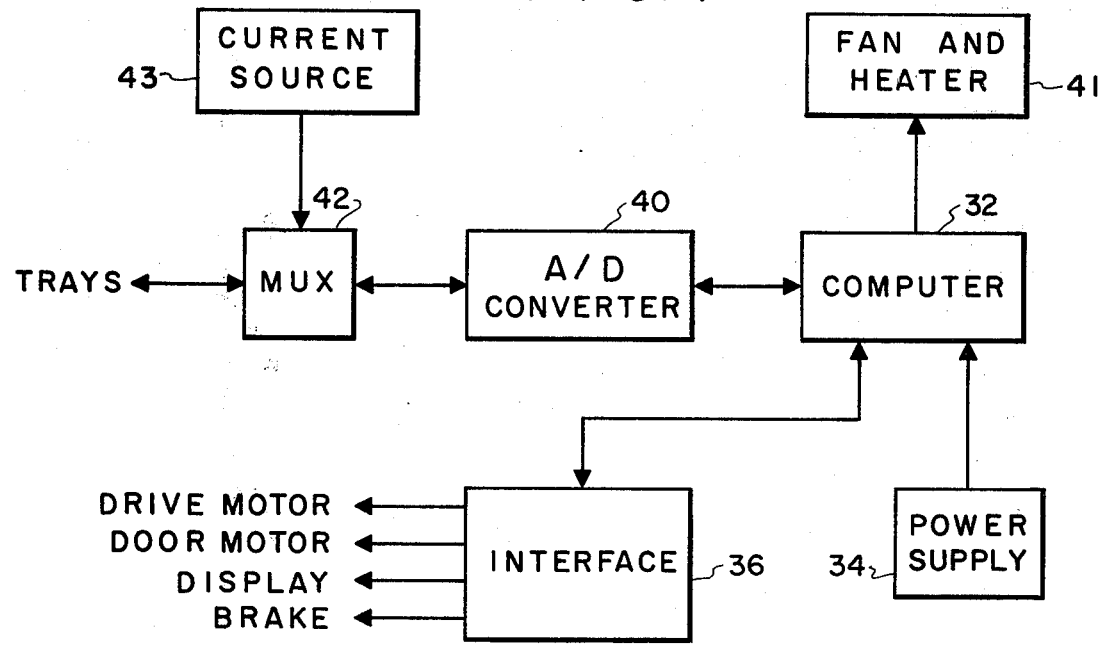
FIG. 4 is a block diagram of the electronic control system for the apparatus constructed in accordance with the present invention.

In FIG. 4 there is illustrated, in block diagram form, a control system for the present apparatus. A microprocessor or computer 32 controls the operating functions of the system in accordance with an established program. A power supply 34 in connected to energize the computer and, through the computer, the other features of the apparatus. The computer 32 is connected to an interface unit 36. The interface unit 36, in turn, effects the control by the computer of the carousel drive motor 30, the door opening motors 21, the control panel and display, and the carousel brake 38. The computer is also connected through an analog to digital converter 40 and a multiplexer 42 to the electrode connections on the carousel trays 12. These electrode connections are shown most clearly in FIGS. 7 and 8. In an exemplary apparatus constructed in accordance with the present invention, the computer 32 included an M6800 microprocessor with the usual complement of RAM's, ROM's and interface units. There is also shown a current source 43 for the excitation of the electrodes 44 in the culture bottles, as well as a fan and heater control 41, controlled by the computer.

In FIG. 7 there is shown a cross-section of a bottle 24 of the type shown and described in the aforementioned copending application, Ser. No. 079,696. The bottle is formed of a clear transparent plastic which is characterized by high mechanical strength and high temperature resistance. A pair of electrodes 44 extend from the rear surface of the bottle into the chamber of the bottle, parallel to each other and to the side walls of the bottle. The electrodes extend through the end wall to form contact points externally of the bottle. The bottle is also provided with a neck eccentrically located with respect to the face of the bottle opposite the surface from which the electrodes protrude. In the arrangement shown, both the neck 46 and the electrodes 44 are completely below the surface level of the fluid content 48 of the bottle 24, when the bottles are placed in the machine.

The receptacle 22 is defined by a pair of sidewalls 50, a rearwall 52 and a bottom 54. The bottom wall 54 of each of the receptacles is provided with two recesses 56, one for each of the two bottles to be placed in each receptacle. The recesses define a forward lip 58. The rear wall 52 is provided with a pair of deep recesses 60 into which is inserted a pair of springlike electrical contact members 62. The contact members 62 are formed in a substantially hairpin shaped structure with the bow of the structure inserted in the recesses 60. One leg of the contact structure 62 comprises an electrical terminal to which suitable leadwire 64 is attached. The other leg of the contact member 62 is formed and positioned to engage the external end of the electrodes 44 to provide an electrical contact with the electrodes 44 and also to apply a measure of spring pressure against the rear surface of the bottle 24. When the bottle is inserted into the receptacle, the spring force causes the forward edge of the bottle to engage the lip 58 at the forward edge of the recess 56 in the receptacle 22, thereby holding the bottle firmly in the receptacle.

The back wall 52 of the receptacle structure includes an extension or vane 66 which projects above the upper surface of the receptacle 22 and is tilted radially inwardly relative to the hub 26 of the carousel tray structure 12. As may be seen in FIGS. 2 and 3, the extension comprises a ring extending above the inner surface of the torus and constitutes an air deflector to assure a uniform flow of warm air past each of the bottles in the incubation chamber.

Figure 5:
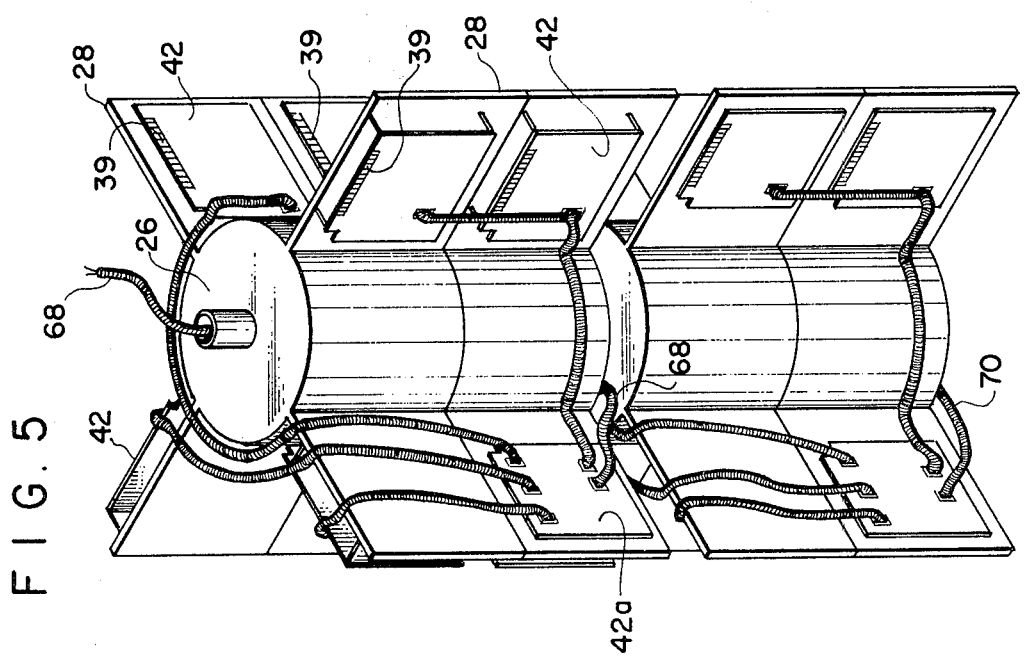
FIG. 5 is a fragmentary view of the support structure of the carousels.

As noted, each of the carousel tray structures 12 includes four of the radial arms 28 which supports the torus or receptacle ring of the carousel 12. In the preferred embodiment, these four radial arms 28 divide the carousel tray into four equal sectors; in the illustrative embodiment each sector includes six receptacles accommodating six pairs of culture bottles. Again, in the preferred embodiment, the lead wires 64 from each of the electrical contact members 62 is connected, for example, to an edge connector 39, to a multiplexor unit 42. Preferably a separate multiplexor unit 42 is provided for the electrical contact members of each of the sectors in each of the carousel members 12. As illustrated in FIG. 5, the multiplexor units 42 are mounted on the radial arms 28. The four illustrated carousel trays are arranged in sets of two with the upper set of two being operated as a unit and the lower set of two being operated as a unit. With no relative motion between the two carousels of the upper unit, the individual multiplexors 42 may be coupled together with a suitable electrical harness to provide an appropriate, addressable, connection for all of the multiplexor units in the upper set of carousel trays to a further multiplexor 42. An interconnect cable 68 is connected to the last of the multiplexor 42a and passes through the assembled hubs. The connector cable 68 is then connected through the A to D converter 40 to the computer 32. Similarly, the multiplexor units 42 on the lower set of carousel trays are connected together through suitable interconnect cabling and through a cable 70 connected through a further multiplexor, not shown, to the A to D convertor 40 and, thence, to the computer 32.

Within the incubation chamber 4, there is provided an upper plenum 72 and a lower plenum 74. The upper plenum refers to the space between the top of the incubation chamber 4 and upper plenum divider panel 76. The panel 76 has a central circular opening 78 which is slightly larger than the circle defined by the upper edge of the air deflection extensions 66 on the upper carousel. The lower plenum 74 refers to the space between the bottom of the incubation chamber 4 and a lower plenum separator panel 80. Between the lower surface of the upper plenum divider panel 76 and the upper surface of the lower plenum divider panel 80 and surrounding the stack of carousels, there is positioned a substantial cylindrical shroud 82. The inner periphery of the shroud 82 encompasses and is slightly spaced from the outer perimeter of the stack of carousels 12. An opening in the shroud is provided to accommodate the access doors 10. Suitable openings 84 are provided through the lower plenum panel 80 but within the circle defined by the shroud 82 to connect the inner volume of the shroud with the lower plenum 74.

Within the control compartment 6, which is separated from the incubation chamber by a vertical partition 86, there is an electronic package represented by the box 88 and containing the electronic controls illustrated in FIG. 4. Also included within the control compartment 6 is a fan and heater structure 90. The fan and heater assembly 90 is arranged to be functioning whenever the present instrument is operational. The heater element is controlled to maintain the temperature in the incubation chamber at a predetermined temperature of about 37° C. The fan structure is arranged to be in communication with the upper and lower plenum chambers 72 and 74, respectively. Thus, air heated by the heating element of the combination 90 is blown into the upper plenum chamber 72. The heated air in the plenum 72 then flows through the central opening 78 to the carousel stack. The air flow deflection extension or vane 66 on the upper carousel causes a portion of that flow of heated air to be diverted to flow around the culture bottles 24 in the upper carousel. The remainder of the air flows down the central open column which is bridged by the radial arms 28. At the level of each successively lower carousel, the deflecting vane or extension 66 causes a further portion of the air to be circulated about the bottles in its corresponding carousel 12. The air is then drawn through the holes into the lower plenum 74 which is, in turn, in communication with the lower end of the fan assembly 90. The air is then recirculated past the heater element and the upper fan structure into the upper plenum.

As was previously mentioned, the upper set of carousel trays 12 are mechanically coupled together for rotation as a unit. Similarly, the lower set of carousel trays are coupled together for rotation as a unit. The maximum rotation of the carousel sets is limited to slightly less than a full 360°, thus, the driving motor 30 is, of necessity, a reversible motor. A limit stop, not shown, prevents the further rotation of the carousel trays in any one direction. With this limited rotation, the cables 68 and 70 interconnecting the multiplexors to the computer may be wired without the necessity of slip rings or the like. The brake 38, shown in FIG. 3, is under the control of the computer and cooperates with detent notches in the perimeter of the carousel trays. Since the two sets of carousel trays are arranged to be counter-rotating with respect to each other, the brake 38, under the control of the computer will serve to hold one set stationary while the other is indexed during a portion of the program where the one set of trays is rotated for access to the associated access door 10. The brake 38 also serves to securely position the rotated set of carousel trays in the position selected by the computer while the culture bottles 24 are either being loaded into or removed from the receptacle 22 in the carousel or otherwise manipulated. The drive motor 30 is also arranged, under control of the computer to not only drive the carousel trays in order to present selected receptacles at the access doors 10, but also the provide a continuous agitation to both sets of carousel trays at all times when the carousel trays are not being driven to a selected position or clamped in a position with the access door open. The agitation of the contents of the bottles in the controlled temperature environment has been found to significantly increase the growth rate of microorganisms in the culture medium. The operation and positioning of the carousels 12 by the computer 32 is such that the progressive loading of the tray maintains a balance in the load with respect to the distribution of the bottles between the upper and lower carousel sets as well as the distribution of the bottles about each of the carousel trays. By thus maintaining a balanced load in the carousel stack, the counter-rotational agitation motion subjects the housing structure to a minimum of vibration.

The front panel of the control compartment includes a plurality of pushbuttons, electrically interconnected with the computer system for selectively controlling the operation of the apparatus. There is also included on the front panel of the control compartment a display which features a plurality of annunciators and a plurality of digital indicators. Each of the pushbuttons are of the type which includes a selectively operated backlight. A first pushbutton 92 is designated LOAD. When this pushbutton is pressed, the associated light comes on, agitation of the carousel trays stops and an empty receptacle position is rotated to the appropriate door 10. When that receptacle has been positioned at the door, the light 14 adjacent that door is lit and the door is opened. A pair of culture bottles may then be inserted through the open door into the indicated receptacle.

The second pushbutton 94 is indicated with the legend positive. The light behind the positive pushbutton will be intermittantly illuminated whenever the measuring system of the present apparatus has determined that one of the bottles measured has a positive micro-organism growth rate above a predetermined threshold level. When that pushbutton 94 is then pressed, the computer causes the agitation of the carousels to stop. The carousel tray carrying the detected positive bottle is rotated until the positive bottle pair is presented to the door 10 associated with that carousel. The door is opened and indicated bottle pair may then be removed for further processing outside of the incubator for a determination of the specific micro-organism involved. If, when that positive bottle pair has been removed, no other positive bottles are present, the door will close and the agitation will be automatically resumed. If, on the other hand, there are other positive bottles present, the process will continue and successive positive bottles will be presented until all such positive bottles have been removed.

The third pushbutton 96 is indicated with the legend EXPIRED. In accordance with the present invention, the apparatus is programmed to provide a predetermined maximum incubation period, e.g., seven days. Under the incubation techniques set forth herein, any detectable micro-organism growth that would have taken place, would have occurred before the end of the seven-day incubation period. Therefore, at the end of a seven day incubation period, the operator will press the EXPIRED pushbutton, the agitation of the carousels will stop and the carousel trays will be rotated to present, serially, the expired bottles at the doors for removal. This operation will continue until all expired bottles have been removed. It will be appreciated that, when the bottles were loaded into the machine, the computer keeps track of the day and loading order of the culture bottles.

The fourth pushbutton 98 bears the legend SEARCH. This pushbutton allows the operator to access any particular bottle in the incubator at any time for bottle subculturing or removal. As was previously mentioned, when the bottles are loaded into the apparatus, the computer keeps track of the order of loading and the location of the bottles. The order of the loading is noted in terms of the day age of a particular group of bottles and the serial order of the bottles in that group. When the SEARCH button is pressed, the light behind that button begins to flash. This button is used in conjunction with the fifth pushbutton 100 which bears the legend STATUS DAY/AGE, as well as a portion of the digital indicator display. A first element 102 of the digital display presents a number representative of the DAY/AGE of a culture bottle which then occupies a selected position in the apparatus. A second element 104 of the digital display presents a three digit number representing a culture number, or the serial order, of a particular culture bottle inserted on the indicated day. These are the two portions of the digital display that are used in conjunction with the SEARCH pushbutton. When the SEARCH pushbutton is pressed, the DAY/AGE indicator and the culture number indicator 102 and 104 are set by the computer to zero, at which point the light behind the pushbutton 100 begins to flash. The pushbutton 100 is then pressed and the DAY/AGE indicator 102 begins to increment until the DAY representing the desired bottle is achieved. When the desired DAY/AGE number appears in the indicator 102, the pushbutton 100 is released. It will remain lit but will cease flashing. If now, the SEARCH 98 is again pressed and held in, the culture number appearing in the digital indicator segment 104 will be incremented by the computer until the desired number appears. When the SEARCH button is released, the light therebehind will cease flashing, agitation of the carousels will stop, the appropriate carousel tray will be rotated and light adjacent one of the doors will be lit and the door will open presenting the selected bottle pair for either removal or subculturing. When the desired functioning has been accomplished, the operator may search for another bottle by again depressing the SEARCH button or terminate the SEARCH sequence. The SEARCH sequence is terminated by simultaneously pressing both the SEARCH and the STATUS DAY/AGE buttons.

In addition to the STATUS DAY/AGE button 100 being used in conjunction with the SEARCH button as set forth above, it may also be used separately to display incubation temperature and the number of available spaces left in the incubator. In this regard, a third portion 106 of the digital display will be brought into operation. This portion of the digital display carries the legend of POSITIVE TIME/TEMPERATURE. If the pushbutton 100 alone is pressed, the button itself will be illuminated and the appropriate numbers will be displayed in the display indicators. The temperature of the air in the incubator will be displayed in the display portion 106.

A further function of the display portion 106 occurs when the instrument indicates that a positive reaction has been detected in at least one of the bottles. When the light behind the PUSHBUTTON 94 begins to flash indicating that a positive reaction has been detected, the display section 106 will indicate the time of day at which such positive reaction was detected. When the positive reaction has been detected and the PUSHBUTTON 94 pressed to index the detected bottle for presentation to one of the access doors, an annunciator 108 will announce whether it is the aerobic or anaerobic bottle in which the positive reaction occurred.

A further annunciator panel 110 includes a number of annunciator elements. Each of these annunciator elements are controlled by the computer and indicate a condition requiring the operator's attention. The first segment bears the legend BOTTLE OUT OF RANGE and indicates that, for one reason or another, a pair of bottles cannot be correctly monitored by the unit. These bottles may then be presented to the appropriate access door 10 and removed for manual incubation and monitoring. A second annunciator segment bears the legend LOAD ERROR. This indicates that one or both bottles have not been properly connected. These bottles must be removed from the receptacle and placed in another receptacle or manually incubated. A third annunciator segment bears the legend LOW TEMPERATURE and is illuminated to warn the operator that a decrease in the incubator temperature has occurred. If the change is less than 1° C., the system can adjust measurement readings accordingly. If the decrease is greater than 1° C., another annunciator, bearing the legend MANUAL INCUBATION will alert the operator to empty all bottles from the apparatus and place them in a manual incubator.

A fifth annunciator segment bears the legend HIGH TEMPERATURE. This annunciator alerts the operator to a major instrument failure. The bottles must be removed immediately from the incubator to a manual incubator to avoid damage to the specimens. A sixth annunciator segments bears the AGITATOR FAIL. When this annunciator is illuminated by the computer, it is indicative that there has been a failure in the motor control circuit.

A seventh segment of the annunicator panel 110 bears the legend MACHINE FULL. When an attempt is made to load additional bottles into the machine when the load pushbutton 92 is pressed the machine attempts to index an empty receptacle in one of the carousel trays 12 to one of the access doors. If there are no acceptable empty receptacles, the MACHINE FULL annunicator will be lit. When this occurs, the operator may choose to incubate the new bottles manually or in another instrument or, alternatively, the operator may request the instrument to terminate at the incubation of a group of bottles a day early. The machine is programmed to accommodate such an early termination. Pressing the EXPIRED button will then present the oldest set of bottles to the appropriate access doors for removal.

An eighth annunicator segment bears the legend BOTTLE PREVIOUSLY REMOVED. When the machine is operated in the search mode, or in an expired mode, when a selected receptacle has been presented to the access door for the removal of the bottles, if the bottle has already been removed from that days sequence of entrys in a previous search or expired operation, the annunicator will inform the operator.

Figure 12:
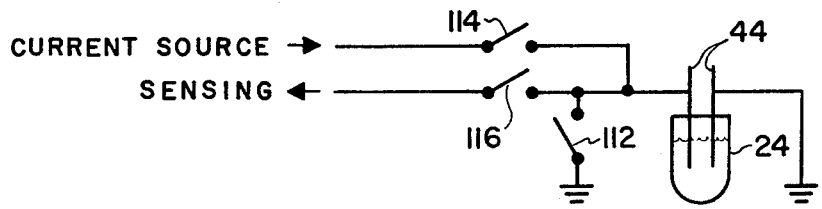
FIG. 12 is a schematic circuit diagram illustrating the operation of a feature of the present invention.

In FIG. 12 there is shown a schematic representation of the measuring system for the present invention. There the culture bottle 24 is shown with one of the electrodes 44 connected directly and permanently to ground. The other electrode is connected to a first selectively operable switch member 112. The switch 112 is arranged, when closed, to connect that other electrode also to ground. A second selectively operable switch 114 is connected between that same electrode and a source of excitation current. A third selectively operable switch 116 is connected between that same electrode and the voltage measuring or sensing circuit. The switches 112, 114 and 116 are all selectively controlled by the microprocessor or computer 32.

Figure 10:
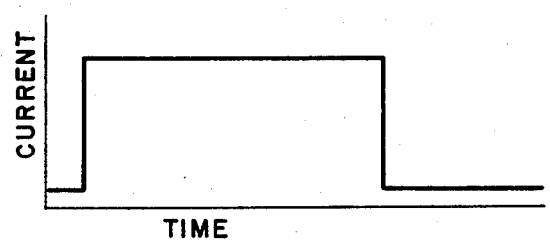
FIGS. 10 and 11 are response curves useful in understanding the present invention.
Figure 11:
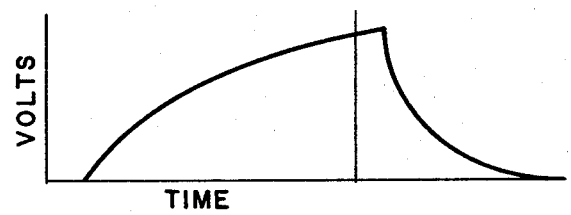

To effect a measurement of the activity of the content of the bottle 24, the switch 12 is momentarily closed. The closure of the switch 112 connects both electrodes 44 in the bottle 24 to ground, thereby assuring that both electrodes in the bottle are at the same potential. The switch 112 is then opened and, simultaneously, the switches 114 and 116 are closed. The closure of the switch 114 allows the computer 32 to apply a constant current signal from the source 43 in the control package 88, to the ungrounded electrodes 44 of the bottle 24. The closure of the switch 116 connects the ungrounded electrode 44 to the input of a high input-impedance voltage detecting circuit. If there is, in fact, no bottle 24 inserted in the receptacle being tested or if there is a bad contact with that bottle, the electrodes will appear to be open circuited and the effective leakage current from the constant current source will be reflected through the high input impedance of the voltage detector circuit. The computer will then translate that voltage signal to effect an illumination of the LOAD ERROR ANNUNICATOR. If on the other hand a proper bottle is inserted in the receptacle, there will be an initial very low voltage drop across the electrodes of the bottle which will signify to the computer through the voltage detector that a proper bottle is in place. As the constant current continues to be applied to the electrodes 44, a charge will be built up across the electrodes to produce an increasing voltage drop across those electrodes. That voltage drop is reflected back to the voltage sensing apparatus through the closed switch 116. In an actual embodiment, the constant current pulse is about 50 milliseconds in duration. A curve representing the application of the constant current pulse to the electrodes is shown in FIG. 10. In FIG. 11 there is illustrated a curve representative of the voltage change resulting from the charging and discharging of the electrodes 44. As the voltage curve riser near its peak, and at a point which is approximately 40 milliseconds, in the referenced embodiment, after the beginning of the constant current pulse, the computer samples the voltage level at the voltage detector. The magnitude of that voltage is a function of the electro chemical characteristic of the fluid in the culture bottle 24. That characteristic, in turn, is a function of the growth of the micro-organisms in the culture. In accordance with the present embodiment, under the control of the computer, the voltage level across each bottle is sampled at one hour intervals, and the last previous value stored in the computer's memory. The sampled voltage is compared with the voltage level of the previous sampling of the same bottle. If the rate of change in the sampled voltage exceeds a predetermined value, the computer will identify that bottle as a positive growth bottle. When that detection is made, the condition is announced by the flashing illumination of the light behind the POSITIVE PUSHBUTTON 94. The procedure for removing the POSITIVE BOTTLE may then be instituted as hereinbefore noted. At the end of the current excitation pulse period, the switches 114 and 116 are opened by the computer and the switch 112 is closed until the next scan cycle for that particular bottle. Folowing that routine, the computer sequentially energizes and reads the status of each of the bottles in each of the carousels in the incubation chamber. Whereas in previous manual incubation and testing techniques, all of the specimens were subjected to subculturing or specific identification analysis, in the present system only those bottles which have been identified as having a positive micro-organism growth need be subjected to the identifying analysis. This clearly effects a considerable saving of time and effort and energy in the diagnosis of a patient.

Thus, there has been provided, in accordance with the present invention, an improved micro-organism growth detection apparatus wherein the micro-organism culture is incubated and the growth of the micro-organisms therein detected automatically without reliance upon human judgement, which system is accurate, reliable and fast in operation.

The embodiments of the invention in which an exclusive property or privilege is claimed are defined as follows:

1. Medical analyzing apparatus including a micro-organism incubator and growth detection apparatus wherein micro-organism cultures are contained in culture bottles having a pair of electrodes for sensing the electrical characteristic of the culture as a function of micro-organism growth, said apparatus comprising in combination:

means defining an incubation chamber;
    a plurality of carousel trays each providing receptacles for a plurality of the aforesaid micro-organism culture bottles, said carousel trays including electrical contact means for contacting the electrodes of each culture bottle positioned in said receptacles; said electrical contact means exerting a spring force to retain said bottle in said receptacles;

driving means operable to impart an oscillatory motion to said carousel trays whereby to agitate the contents of said culture bottles in said incubation chamber;

a plurality of selectively operable doors providing access to said incubation chamber, said doors corresponding in number to said plurality of carousel trays and positioned, respectively, to access the receptacles of an associated tray, said driving means being further operable to selectively index said trays to present a selected receptacle for access at its associated door; and a micro-computer means connected to control said driving means and said doors, said micro-computer also being connected to periodically sample the electrical characteristics of said culture bottles in said incubator chamber, whereby to detect growth of micro-organisms in said bottles as a function of changes in said electrical characteristic.

2. Medical analyzing apparatus as set forth in claim 1 wherein means are provided for causing a controlled flow of warm air through said incubation chamber and distributed about said culture bottles to provide an atmosphere conducive to a rapid growth of micro-organism in said bottles.

3. Medical analyzing apparatus as set forth in claim 2 wherein said last mentioned means includes a fan and heater combination, said heater being controlled to maintain said air in said incubation chamber at a predetermined temperature.

4. Medical analyzing apparatus as set forth in claim 2 and including a control and display panel having control buttons and display elements electrically connected to said micro-computer for the selective control of said apparatus.

5. Medical analyzing apparatus as set forth in claim 4 wherein said display elements include digital indicator means for indicating selected parameters relative to the operation of said apparatus.

6. Medical analyzing apparatus as set forth in claim 5 wherein said display elements include annunicators connected to be controlled by said micro-computer means to indicate determined selected abnormalities in the operation of said apparatus.

7. Medical analyzing apparatus as set forth in claim 6 wherein multiplexer means are mounted on said carousel trays and connected to selectively couple said electrical contact means with said micro-computer means, said micro-computer means being operative to periodically and sequentially sample the electrical impedance across said electrodes in said bottles as a function of micro-organism growth and to activate said display elements to indicate the presence of a positive growth in at least one of said bottles.

8. Medical analyzing apparatus as set forth in claim 3 wherein each of said carousel trays includes a plurality of receptacles for said bottles forming a torus about a central hub, said torus being supported from said hub by a plurality of radial arms and forming an open column for the flow of said air, each said torus having a deflecting vane extending into said column to deflect a portion of said warm air around each of the bottles in the associated tray.

9. Medical analyzing apparatus as set forth in claim 8 wherein multiplexer means are mounted on said radial arms of the carousel tray assemblies and connected to selectively connect said electrical contact means associated, respectively, with said culture bottle electrodes to said micro-computer means.

10. Medical analyzing apparatus as set forth in claim 2 wherein said plurality of carousel trays are arranged in two sets with an equal number of trays in each set, said sets of carousel trays being driven in counter-rotational relation during said oscillatory motion mode whereby to minimize vibration of the apparatus.

11. Medical analyzing apparatus as set forth in claim 2 wherein said carousel trays are arranged to be driven in an indexing mode through an angular displacement of slightly less than 360°, a limit stop preventing further rotation.

12. Medical analyzing apparatus as set forth in claim 11 wherein said carousel trays are operated in said oscillatory motion mode and said indexing mode selectively and alternatively under the control of said micro-computer means.

13. Medical analyzing apparatus as set forth in claim 12 wherein brake means are provided for clamping one set of carousel trays in fixed position while the other of said sets of carousel trays is being indexed to the selected position, said brake means being further operable to clamp said other set of carousel trays in said selected position, said brake means being selectively operable in response to control signals from said micro-computer means.

14. Medical analyzing apparatus as set forth in claim 13 wherein the selected one of said doors is controlled by said micro-computer to be opened when said selected receptacle has been indexed for access.

15. Medical analyzing apparatus as set forth in claim 14 wherein each of said doors includes an operating arm, a driving member operatively connected to said arm and a driving motor means, said motor means being connected to be selectively operable in response to control signals from said micro-computer means.

16. Medical analyzing apparatus as set forth in claim 15 wherein a signal light is provided adjacent each of said doors, said light being connected to be responsive to control signals from said micro-computer means to be illuminated whenever the adjacent door is programmed to be opened by said micro-computer.

* * * * *